US00PP29041P3

(12) United States Plant Patent
Kordes

(10) Patent No.: US PP29,041 P3
(45) Date of Patent: Mar. 6, 2018

(54) MINIATURE ROSE PLANT NAMED 'KORAROMA03'

(50) Latin Name: *Rosa hybrida*
Varietal Denomination: KORaroma03

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Offenseth-Sparrieshoop (DE)

( * ) Notice: Subject to any disclaimer, the term of this patent is extended or adjusted under 35 U.S.C. 154(b) by 52 days.

(21) Appl. No.: 15/330,043

(22) Filed: Jul. 29, 2016

(65) Prior Publication Data

US 2018/0035584 P1 Feb. 1, 2018

(51) Int. Cl.
*A01H 5/02* (2006.01)

(52) U.S. Cl.
USPC ..... Plt./120

(58) Field of Classification Search
USPC ..... Plt./120
See application file for complete search history.

*Primary Examiner* — Keith O Robinson
(74) *Attorney, Agent, or Firm* — Samuel R. McCoy, Jr.

(57) ABSTRACT

'KORaroma03' is a new and distinct variety of *Rosa hybrida* which is characterized by the combination of a compact and upright growth habit, a moderately vigorous rate of growth, very good resistance to *Botrytis* and powdery mildew rose diseases, panicles bearing two to four cream apricot flowers, double flowers, and flowers with a strong classic rose fragrance. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORaroma03'.

STATEMENT REGARDING PRIOR DISCLOSURES BY THE INVENTOR UNDER 37 C.F.R. 1.77(B)(6)

The first public disclosure of the claimed plant was made in January of 2016 at the 2016 IPM horticulture tradeshow in Essen, Germany where it was displayed by the inventor amongst a collection of other rose cultivars. The claimed plant was not specifically identified by name in the display. 'KORaroma03' was not publically available or sold prior to one year before the date of the instant application.

BACKGROUND OF THE INVENTION

Parentage: The *Rosa hybrida* variety 'KORaroma03' is the result of a controlled cross-pollination breeding program carried out by the inventor in Klein Offenseth-Sparrieshoop, Germany. The objective of the said breeding program was to create a new and distinct rose plant with unique qualities, such as:

1. Compact and uniform growth and uniform flowering when grown as a potted floral plant; and
2. Abundant, long-lasting, and recurrent cream apricot flowers; and
3. Attractive foliage; and
4. Resistance to diseases encountered in greenhouse and nursery culture.

This combination of qualities is not present in prior rose cultivars known to the inventor. These objectives have been substantially achieved and in that distinguish 'KORaroma03' from all other varieties known to the inventor.

'KORaroma03' is a seedling selection which resulted from the controlled pollination of an unnamed *Rosa hybrida* seedling developed and owned by the same inventor, the seed parent, with a second unnamed *Rosa hybrida* seedling developed and owned by the same inventor, the pollen parent, during the summer of 2012. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2013 from the seedling beds due to its superior characteristics and asexually propagated for further evaluation. This new and distinctive rose variety was given the name 'KORaroma03'.

Asexual Reproduction: 'KORaroma03' was first asexually propagated by bud grafting in June of 2013 at the inventor's nursery in Klein Offenseth-Sparrieshoop, Germany. Subsequently, 'KORaroma03' has been successfully propagated by stem cuttings in Jackson County, Oreg. These initial and other subsequent propagations conducted in controlled environments demonstrate that 'KORaroma03' reproduces true to type in successive generations of asexual reproduction.

SUMMARY OF THE INVENTION

The following characteristics have been repeatedly observed and represent the distinguishing characteristics of the new *Rosa hybrida* cultivar 'KORaroma03'. These traits, in combination, distinguish 'KORaroma03' as a new and distinct cultivar.

1. *Rosa hybrida* 'KORaroma03' exhibits a moderately vigorous growth rate; and
2. *Rosa hybrida* 'KORaroma03' exhibits a compact, upright growth habit; and
3. *Rosa hybrida* 'KORaroma03' exhibits very good resistance to *Botrytis* and powdery mildew diseases; and
4. *Rosa hybrida* 'KORaroma03' exhibits panicles of 2 to 4 cream apricot flowers held upright; and
5. *Rosa hybrida* 'KORaroma03' exhibits double flowers of medium size for a miniature rose; and
6. *Rosa hybrida* 'KORaroma03' exhibits flowers with a strong classic rose fragrance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORaroma03', taken from a 15 month old plant.

DETAILED BOTANICAL DESCRIPTION

The following is a detailed botanical description of a new and distinct variety of *Rosa hybrida* known as 'KORaroma03', based upon observations made in May of 2016 from 15 month old, greenhouse-grown container plants in Jackson County, Oreg. Those skilled in the art will appreciate that certain characteristics will vary with older or, conversely, with younger plants. 'KORaroma03' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORaroma03' and comparisons with the parents and closest known comparator variety of *Rosa hybrida* are provided below.

General plant description:

*Growth rate*.—Moderately vigorous.

*Growth habit*.—Compact, upright.

*Mature dimensions*.—25 cm tall and 20 cm wide, when grown as a 17 cm pot plant.

*Cold hardiness*.—Unknown.

*Propagation*.—Stem cuttings and bud grafting.

*Disease resistance*.—Very good resistance to powdery mildew (*Sphaerotheca pannosa*) and *Botrytis* diseases under normal growing conditions in Jackson County, Oreg.

Root system:

*Type*.—Fibrous root system.

*Branching*.—Freely branched.

*Density*.—Moderately dense.

*Distribution*.—Roots distributed evenly throughout the soil profile, from shallow to deep.

Stems:

*Stem color*.—Young stems are Yellow-Green Group 146C; mature stems are Yellow-Green Group 146A.

*Anthocyanin intonations*.—None.

*Stem surface texture*.—Both juvenile and mature stems are smooth.

*Stem dimensions*.—Typical mature stems are approximately 35 cm long and 3 to 5 mm in diameter.

*Prickles*.—Incidence — Typically 5 prickles per 10 cm of stem, on average. Size — Average length is 5 mm long. Immature prickle color — Greyed-Yellow Group 160D. Mature prickle color — Yellow-Green Group 146C, with anthocyanin intonations of Greyed-Orange Group 174C. Shape — Linear. Texture — Smooth.

Leaves:

*Arrangement*.—Imparipinnate compound leaves; mature axillary leaves typically with 5 leaflets, yet leaves with 7 leaflets are regularly observed. Pinnately compound leaves with 4 leaflets are also occasionally observed.

*Attachment*.—Petiolate.

*Dimensions*.—120 mm long and 90 mm wide.

*Abundance*.—Average; 20 to 25 leaves on average.

*Stipules*.—Size — 20 mm long and 5 mm wide. Stipule color — Yellow-Green Group 146A. Anthocyanin intonations — None. Stipitate glands — A limited number of stipitate glands are present on the margins. Margins — Serrulate, with stipitate glands. Texture, adaxial surfaces — Rugose. Texture, abaxial surfaces — Glabrous. Apex — Apiculate. Base — Fused to the petiole.

*Petiole*.—Length — Average 10 mm. Diameter — Average 2.0 mm. Petiole color, adaxial surface — Yellow-Green Group 146B. Petiole color, abaxial surface — Yellow-Green Group 146A. Anthocyanin intonations — None. Margins — With stipitate glands and fine hairs. Prickles — Small prickles are present on the abaxial surface. Stipitate glands — A limited number of stipitate glands are present. Texture — Glabrous. Strength — Strong.

*Rachis*.—Length — Average 20 mm. Diameter — Average 1.5 mm. Color — Yellow-Green Group 146C. Anthocyanin intonations — None. Margins — With very few stipitate glands. Prickles — A few small prickles on the abaxial surface. Stipitate glands — A limited number of stipitate glands and a limited number of fine hairs are present. Texture — Glabrous.

*Leaflets*.—Dimensions — Average size of the terminal leaflet is 45 mm long and 30 mm wide. Shape — Ovate. Apex — Acute. Base — Obtuse. Margins — Finely serrated; not undulated. Texture, pubescence, and luster; adaxial surface — Leathery, glabrous, and semi-glossy. Texture, pubescence, and luster; abaxial surface — Leathery, glabrous, and matte; small prickles present. Juvenile foliage color, adaxial surface — Yellow-Green Group 146B. Juvenile foliage color, abaxial surface — Yellow-Green Group 146C. Mature foliage color, adaxial surface — Green Group 137A. Mature foliage color, abaxial surface — Yellow-Green Group 147B. Anthocyanin intonations — Intonations of Greyed-Red Group 182A are present on both surfaces of the juvenile foliage, and also the upper surfaces of the juvenile rachis and petiole. Venation — Reticulate. Petiolule — Dimensions — 2.0 mm long and 1.0 mm in diameter. Petiolule color, adaxial surface — Green Group 137C. Petiolule color, abaxial surface — Yellow-Green Group 147B. Prickles — A few small prickles are present on the abaxial surface. Texture, adaxial surface — Smooth. Texture, abaxial surface — Leathery.

Inflorescence:

*Inflorescence type*.—Panicles which bear 2 to 4 flower buds. Flowers are held upright.

*Blooming habit*.—Recurrent; floriferous.

*Size*.—10 cm tall and 12 cm wide, on average.

*Peduncle*.—Length — 40 to 70 mm average length. Diameter — 2.0 to 3.0 mm average diameter. Color — Yellow-Green Group 144A. Anthocyanin intonations — None. Strength — Strong. Surface — Smooth; glabrous.

Flowering laterals: Present below the initiation of inflorescence. Generally 2 flowering laterals are present, with 1 to 2 flowers per flowering shoot.

Flower bud:

*Bud form*.—Long; pointed ovoid.

*Size*.—Upon opening, 35 mm in length from base of receptacle to distal end of bud and 20 mm diameter at its widest point.

*Texture*.—Smooth.

*Color, as sepals first unfold*.—Red Group 49B.

*Color when one-quarter open, inner side*.—Red Group 37C.

*Color when one-quarter open, outer side*.—Red Group 36C.

Flower:

*Pedicel*.—Length — 40 to 60 mm average length. Diameter — 2.0 to 3.0 mm average diameter. Color — Yellow-Green Group 146A. Anthocyanin intonations — None. Strength — Strong. Surface — Rugose, with fine hairs and stipitate glands.

*Calyx*.—General — Comprised of five polysepalous sepals, with moderate foliaceous appendages present on three sepals. Diameter of calyx — 50 mm, at anthesis. Sepals — Color, upper surface — Yellow-Green Group 147C. Color, lower surface — Yellow-Green Group 146B. Anthocyanin intonations — None. Size — 20 mm long and 8 mm wide, on average. Apex — Typically apiculate and occasionally cirrose. Base — Flat at union with receptacle. Quantity — Five. Upper surface — Pubescent. Lower surface — Occasionally with stipitate glands. Margins — Pubescent; stipitate glands are present. Stipitate glands, occurrence — Moderate.

*Corolla*.—Habit — Double. General shape of corolla — Cup-open; shallow. Shape of corolla when viewed from the side — Upon opening, upper portion — Flattened convex. Upon opening, lower portion — Flattened convex. Open flower, upper portion — Flat. Open flower, lower portion — Flattened convex. Dimensions — Medium size for a miniature rose. When open, the average flower diameter is 45 mm and the average flower height is 25 mm. Fragrance — Strong fragrance; best described as a blend of classic rose and apple. Duration — On the plant for 8 to 10 days; 3 to 5 days as a cut flower. Senesced petals clinging. Petals — Petal count — Exhibits double flowers with an average of 40 to 50 petals under normal conditions. Petal reflex — Petals are somewhat reflexed. Timing of petal reflex — Simultaneous. Petal margin — Entire. Petal shape — Obovate. Apex — Obtuse. Base — Obtuse. Dimensions — 20 to 30 mm long and 12 to 30 mm wide. Texture, inner surface — Smooth. Texture, outer surface — Smooth. Petal color, upon opening — Outermost petals, inner surface — Red Group 56C. Outermost petals, outer surface — Red Group 56D. Innermost petals, inner surface — Red Group 37C. Innermost petals, outer surface — Red Group 37B. Basal petal spots, upon opening — Outermost petals — Color, inner surface — Yellow Group 3C. Color, outer surface — Yellow-Green Group 154D. Dimensions — 3 mm wide and 5 mm tall. Innermost petals — Color, inner surface — Yellow Group 2B. Color, outer surface — Green-Yellow Group 1B. Dimensions — 3 mm wide and 4 mm tall. Petal color, after opening — Outermost petals, inner surface — White Group N155C. Outermost petals, outer surface — White Group N155D. Innermost petals, inner surface — Orange Group 29C. Innermost petals, outer surface — Red Group 37C. Basal petal spots, after opening — Outermost petals — Color, inner surface — Yellow Group 3C. Color, outer surface — Yellow Group 2D. Dimensions — 4 mm wide and 5 mm tall. Innermost petals — Color, inner surface — Yellow Group 4B. Color, outer surface — Yellow Group 3B. Dimensions — 4 mm wide and 3 mm tall. General Tonality — On open flower, Red Group 37D. No change in general tonality at the end of the seventh day; thereafter the general tonality is Red Group 36D. Petaloids — Quantity — 20 petaloids per flower, on average. Dimensions — Variable; approximately 10 to 18 mm long and 3 to 8 mm wide. Color, inner surface — Marginal Zone — Orange Group 29C. Middle Zone — Orange Group 29C. Basal Zone — Yellow Group 3C. Color, outer surface — Marginal Zone — Red Group 36A. Middle Zone — Red Group 36A. Basal Zone — Yellow Group 3D. Margins — Entire to undulated. Shape — Highly irregular; obovate to spatulate. Apex — Obtuse. Base — Attenuate to obtuse. Texture, inner and outer surfaces — Smooth.

Reproductive organs:

*Stamens*.—Quantity — Approximately 40, on average, arranged around the styles. Anthers — Shape — Reniform. Dimensions — 4.0 mm long and 2.0 mm wide, on average. Color — Yellow-Orange Group 18C. Pollen — Present; scarce. Color is Yellow-Orange Group 22B. Filaments — Color — Yellow Group 6B. Length — 5 mm.

*Pistils*.—Quantity — Average; approximately 35. Stigmas — Size — 2.0 mm. Location — Slightly superior in position to anthers. Color — Greyed-Yellow Group 160D. Styles — Length — Approximately 6.0 mm long. Color — Yellow-Green Group 145B, with intonations of Red Group 39B to 39C. Ovary — Dimensions — 4 mm long and 5 mm in diameter. Color — White Group 155A.

*Receptacle*.—Shape — Urn-shaped. Dimensions — Approximately 12 mm high and 10 mm wide. Color — Yellow-Green Group 146C. Texture — Smooth.

Hips and seed formation: Not observed.

COMPARISONS WITH THE PARENTS

The new rose plant may be distinguished from its seed parent, an unnamed *Rosa hybrida* seedling, by the following combination of characteristics:

1. 'KORaroma03' exhibits cream apricot flowers, whereas the seed parent exhibits cream white flowers.
2. 'KORaroma03' exhibits flowers of medium size for a miniature rose, whereas the seed parent exhibits small flowers.
3. 'KORaroma03' exhibits a flat flower shape, whereas the seed parent exhibits a globular flower.

The new rose plant may be distinguished from its pollen parent, an unnamed *Rosa hybrida* seedling, by the following combination of characteristics:

1. 'KORaroma03' exhibits cream apricot flowers, whereas the pollen parent exhibits cream white flowers.
2. 'KORaroma03' exhibits flowers of medium size for a miniature rose, whereas the pollen parent exhibits small flowers.
3. 'KORaroma03' exhibits a moderately long shelf life as a potted plant, whereas the pollen parent exhibits a short shelf life as a potted plant.

COMPARISON WITH THE MOST SIMILAR *ROSA* CULTIVAR KNOWN TO THE INVENTOR

For a comparison, several physical characteristics of the *Rosa hybrida* variety 'KORpedia', a rose variety from the same inventor which is described and illustrated in U.S. Pat. No. 19,638, are compared to 'KORaroma03' in Chart 1.

CHART 1

| Characteristic | 'KORaroma03' | 'KORpedia' |
|---|---|---|
| General tonality of the flower. | Red Group 37D. | Yellow Group 2B. |
| Petal count. | 40 to 50. | 34 to 38. |
| Fragrance. | Strong. | Non-fragrant to lightly fragranced. |

That which is claimed:

1. A new and distinct variety of rose plant named 'KORaroma03', as described and illustrated herein.

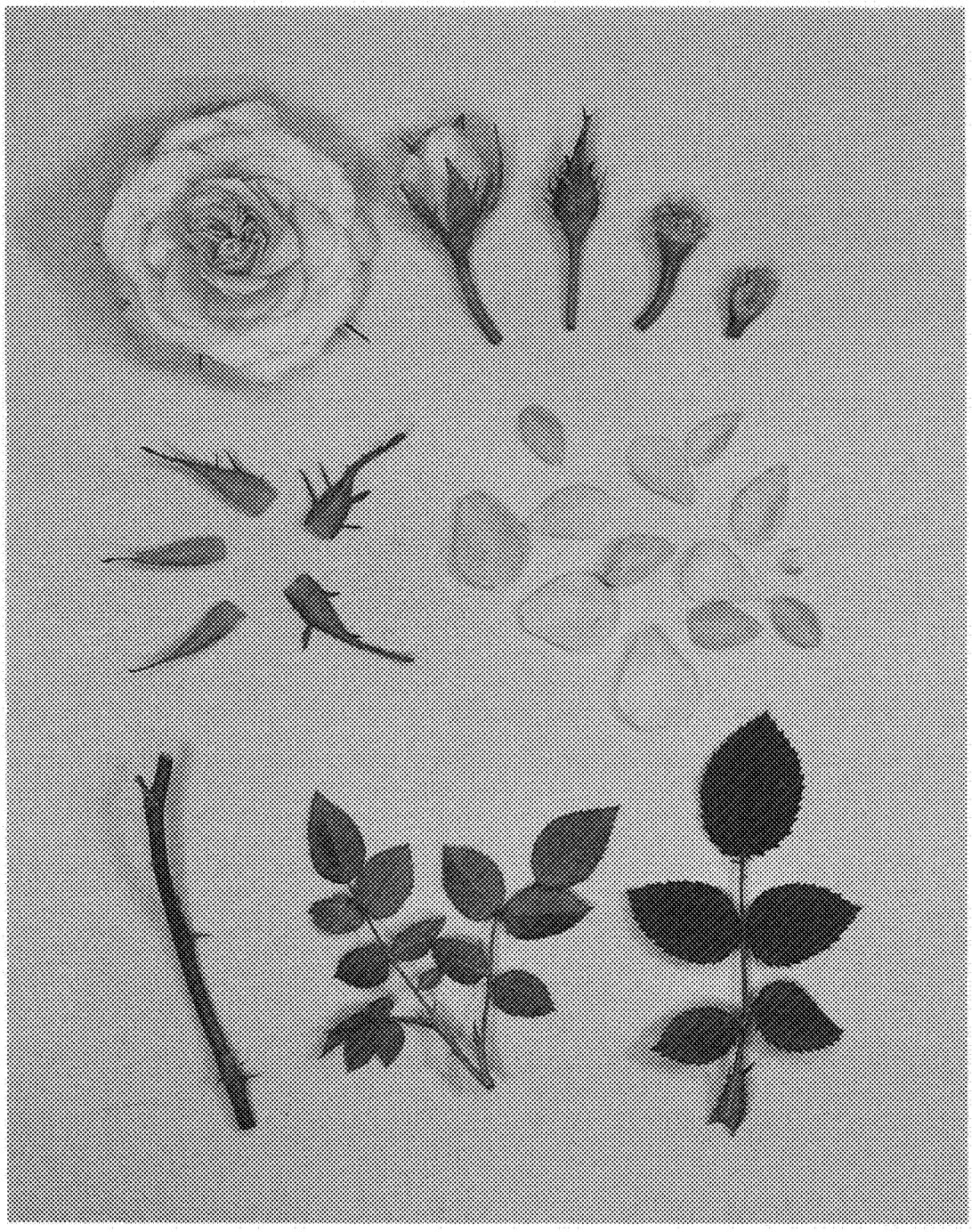

* * * * *